FIP8212  XR  3,970,845

United States Patent [19]
Hollis et al.

[11] 3,970,845
[45] July 20, 1976

[54] PULSE DISCRIMINATOR CIRCUIT
[75] Inventors: David L. Hollis; Richard G. Magner, both of Raleigh, N.C.
[73] Assignee: Corning Glass Works, Corning, N.Y.
[22] Filed: Oct. 23, 1975
[21] Appl. No.: 625,048

[52] U.S. Cl. .............................. 250/214 R; 250/201; 250/209; 250/236
[51] Int. Cl.² .......................................... H01J 39/12
[58] Field of Search ................ 250/201, 206, 214 R, 250/208, 209, 236, 234, 578; 250/222 PC; 356/40, 39

[56] References Cited
UNITED STATES PATENTS

| | | | |
|---|---|---|---|
| 3,390,229 | 6/1968 | 222 PC X .................. | 250/222 X PC |
| 3,463,928 | 8/1969 | Murphy........................... | 250/214 R |
| 3,772,523 | 11/1973 | Montanvert et al. ........... | 250/214 X |
| 3,864,564 | 2/1975 | Adkins................................ | 250/201 |

*Primary Examiner*—Walter Stolwein
*Attorney, Agent, or Firm*—William J. Simmons, Jr.; Walter S. Zebrowski; Clarence R. Patty, Jr.

[57] ABSTRACT

A pulse discriminator circuit for use in a closed loop scanning and positioning system for finding and positioning white blood cells. The surface of a slide is scanned to produce an optical signal which is converted by a sensor into an electrical signal. This signal is applied to the pulse discriminator circuit which provides an output pulse only when a white blood cell is being scanned. The output of the pulse discriminator is coupled to a logic circuit which produces signals that are used to drive the microscope stage to cause the white blood cell to be positioned within a small aperture in the optical system.

6 Claims, 11 Drawing Figures

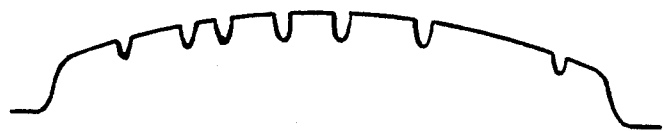
Fig. 3a
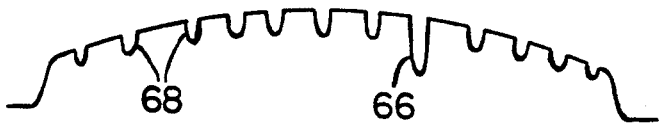
Fig. 3b
Fig. 3c
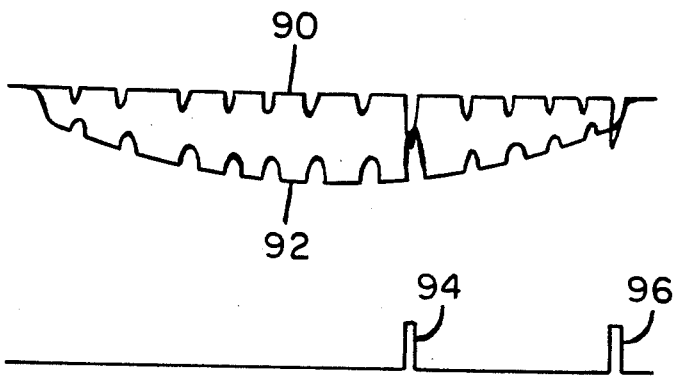
Fig. 3d
Fig. 3e
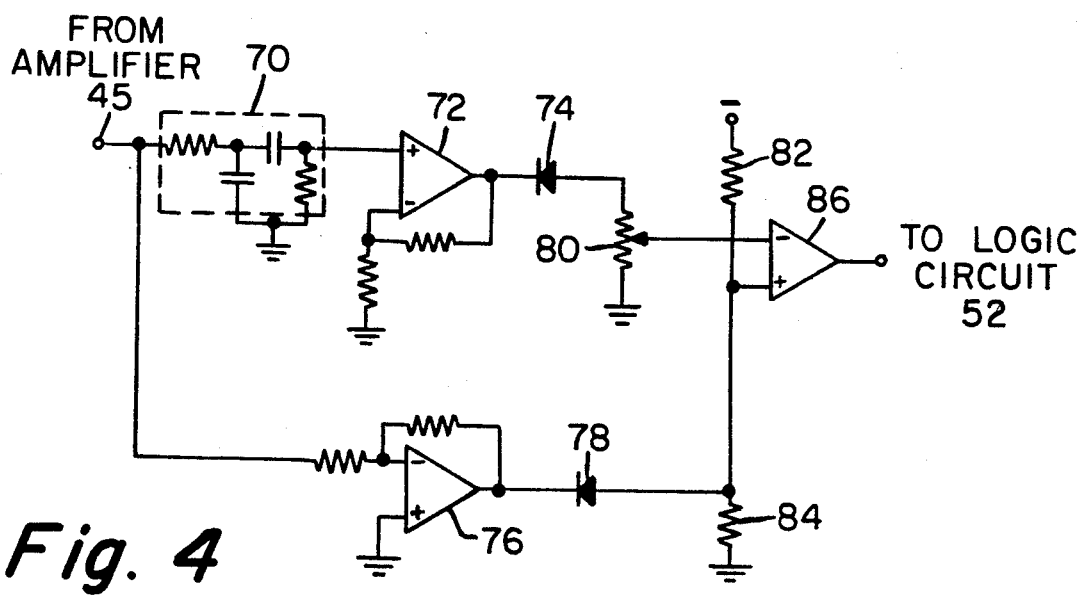
Fig. 4

PULSE DISCRIMINATOR CIRCUIT

BACKGROUND OF THE INVENTION

This invention relates to a system for converting the optical image of a laboratory slide to electrical signals and more particularly to a pulse discriminator circuit employed in an acquisition system for bringing a specimen of interest on the slide into position for analysis.

In the analysis of blood samples, the blood is smeared on a laboratory slide and the smear is stained. By counting the leukocytes on the stained smear, laboratory technicians perform what is referred to as a white blood cell differential. Automation of this differential has significant economic impact because the differential is performed so frequently at every hospital. A thesis by J. W. Bacus, "An Automated Classification of the Peripheral Blood Leukocytes by Means of Digital Image Processing", University of Illinois, Chicago, 1971, describes one automated system.

In a system disclosed in U.S. Pat. No. 3,883,852, D. A. Cotter, a scanning unit (in this case a T.V. camera) linearly sweeps a vidicon target subjected to intense illumination which passes through the smeared slide.

In order to count and classify the blood cells on a slide it is necessary to successively find each blood cell and focus its image on the vidicon target. An automatic focusing system is described in copending application Ser. No. 543,515, filed Jan. 23, 1975, Amos et al. U.S. Pat. No. 3,864,564 issued to W. J. Adkins discloses an acquisition system for successively locating a white blood cell and bringing it into proper position for analysis. That system includes a rotating multifaceted mirror which, in conjunction with a microscope, causes a first light sensor to scan the microscope slide and generate an acquisition signal. A second light sensor receives light pulses from the rotating mirror and generates sync pulses for a logic circuit to which the first sensor is connected. In response to the acquisition and sync pulses, the logic circuit produces signals which are used to drive a microscope stage in x and y directions to cause the white blood cell to be positioned within a small aperture.

Because of the stain used on the blood smear and because of the optical filter disposed in the optical system prior to the acquisition aperture, the white blood cells absorb more light than the red blood cells. Thus, the acquisition signal comprises a series of negatively going pulses superimposed on a positive bias voltage, provided that the first sensor generates a voltage that increases as the intensity of the applied light increases. The pulses generated in response to the white blood cells are ideally more negative than those generated in response to the red blood cells by an amount sufficient to enable a pulse discriminator circuit to readily distinguish between the two and provide an output pulse only in response to the white blood cell. Under such ideal conditions a comparator circuit, which compares the acquisition signal with a predetermined dc level, is adequate.

However, the light is not necessarily uniform over the field, and a red blood cell located at the end of the field can appear almost as dark as a white blood cell located at the center of the field. Also, the total light level seen by the first light sensor can vary such that the overall amplitude of the signal generated thereby also varies. Moreover, the light level across the field can vary considerably if the condenser optics are slightly misaligned. Thus it is possible for a red blood cell in one part of the field to appear as dark as a white blood cell in another part of the field and for the level of either to vary from time to time. Under such adverse conditions a circuit which employs a fixed comparison voltage may not be able to distinguish between pulses produced in response to white and red blood cells.

SUMMARY OF THE INVENTION

The circuit of the present invention is adapted to be employed in an automated slide analyzer. A specimen of interest on the optical slide is positioned with respect to a viewing aperture by a logic circuit which receives signals from light sensing devices. These signals are processed by the discriminator circuit of the present invention to ensure that only pulses generated by a specimen of interest, e.g., a white blood cell, are passed to the logic circuit. A rotating mirror successively scans portions of the optical image of the slide across one of the light sensing devices. The logic circuit produces control signals which are used in positioning of the slide. If no specimen of interest, in this case a white blood cell, is detected during a scan, the logic circuit produces a signal which moves the microscope slide in the y direction, orthogonal to the direction of scanning so that another field of view can be scanned.

The pulse discriminator circuit is characterized in that it comprises a voltage comparator for producing an output signal only when the voltage applied to a first terminal thereof exceeds that applied to a second terminal thereof. The signal from the light sensor is applied directly to an inverting amplifier and is applied to a noninverting amplifier by way of a filter which passes pulses generated by various specimens on the slide such as red and white blood cells while removing the dc background level of the signal. Means are provided for coupling the output of the noninverting amplifier to the first comparator terminal and for coupling the output of the inverting amplifier to the second comparator terminal. The comparator circuit provides an output pulse only during the time that a specimen of interest is being scanned.

The foregoing and other objects, features and advantages of the invention will be better understood from the following more detailed description and appended claims.

DESCRIPTION OF THE DRAWINGS

FIGS. 3A–3E are waveforms of voltages appearing at various points in the system.

FIG. 4 shows an electrical schematic of the pulse discriminator circuit of the present invention.

DESCRIPTION OF THE PREFERRED EMBODIMENT

Figure 1:
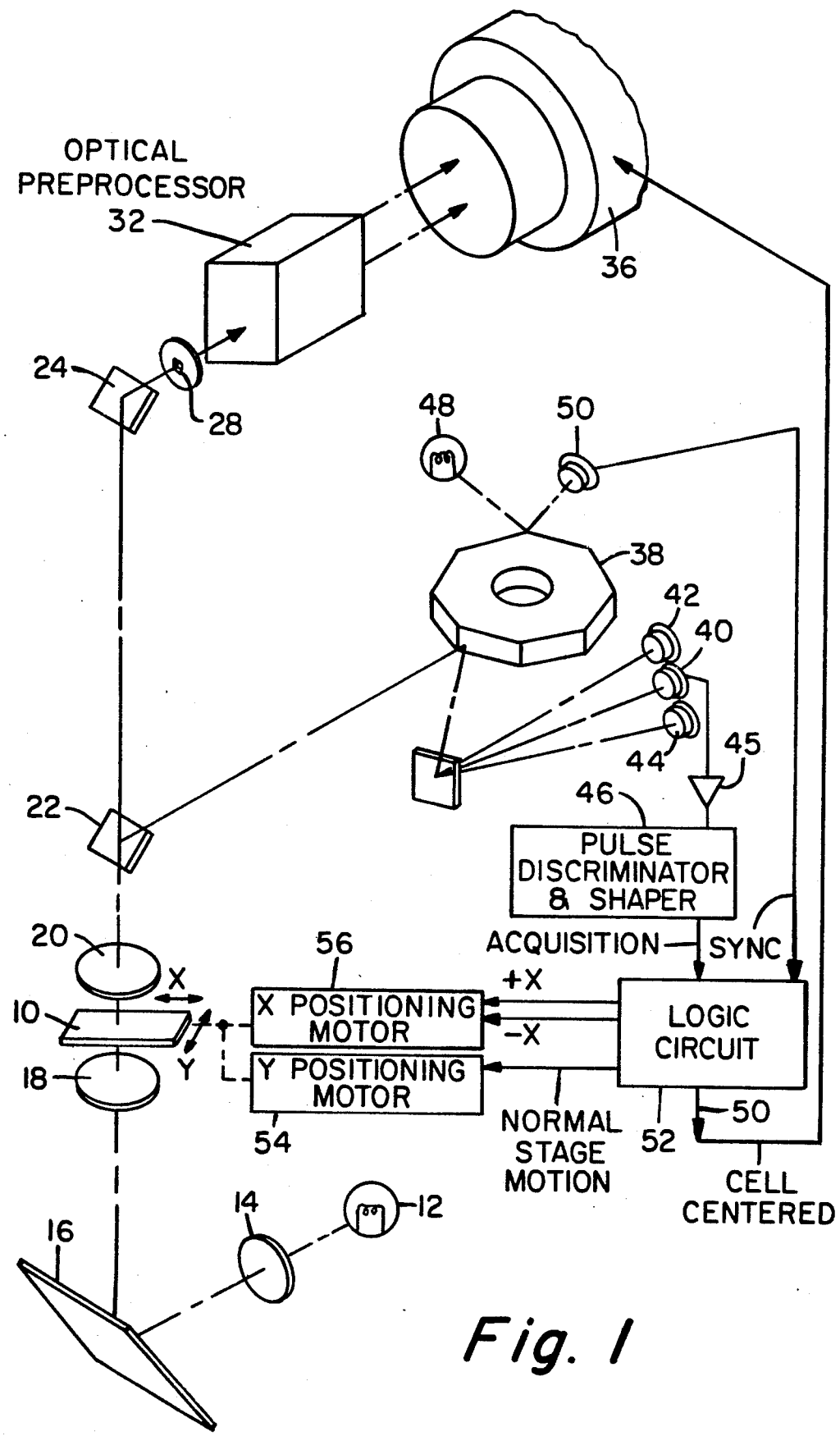
FIG. 1 is an optical and electrical schematic diagram of an acquisition system for slide analysis.

FIG. 1 shows the optics for a system for scanning and counting leukocytes on a blood smeared slide 10. Light from lamp 12 passes through lens 14, is reflected from fold mirror 16, and passes through condenser lens 18. The light passes through slide 10 and is collected by objective lens 20. A first beam splitter 22 reflects approximately 40% of the light to an automatic focus and acquisition system of which this invention is a part. The remainder of light is reflected by mirror 24 to an optical-to-electrical convertor which scans and analyzes a blood cell whose image is centered on aperture 28. The light image passing through aperture 28 is applied to optical preprocessor 32 which may be an optical system of the type disclosed in U.S. Pat. application entitled "Attenuating Image Extender for Multiple Imaging System", Ser. No. 617,417 filed Sept. 29, 1975 Adrian. Optical preprocessor 32 causes contiguous images having different color characteristics to be formed at the target of vidicon type TV camera 36. Electrical signals produced by camera 36 are ultimately converted into digital signals representing the characteristics of each white blood cell. This conversion is more fully described in the aforementioned Cotter patent.

A portion of the focused light from beam splitter 22 strikes a rotating multifaceted mirror 38. Light striking mirror 38 forms an image of the slide which is parfocal with the image applied to the converter. The rotating mirror reflects a portion of the slide image onto a light sensing device 40. Light sensing devices 42 and 44 are used in the focusing system as more fully described in the copending Amos et al. application. A very narrow slice of the slide image is scanned as the mirror 38 rotates. The light sensing device 40 produces an output signal proportional to the light absorption of the area of the slide being scanned. This signal is coupled by amplifier 45 to pulse discriminator and shaper circuit 46 which produces acquisition pulses indicating the detection of white blood cells on slide 10.

A second light source 48 is focused on the rotating mirror 38 and the focused light is swept across a second light sensing device 50. The light sensing device 50 is adjusted so that the light from source 48 strikes it at a predetermined position in the scan. In this case, the light strikes photocell 50 in time relation to the beginning of a scan of the mirror across the slide. The light sensing device 50 produces a synchronizing signal to mark the beginning of the sweep by a given facet.

The acquisition pulses and synchronizing pulses are applied to logic circuitry 52 which is more fully described in the aforementioned Adkins patent. The logic circuitry utilizes these pulses to determine if a specimen of interest is in the field of view of one of the scanning segments. If so, the circuitry determines which way the stage must move in order to center the specimen in the aperture. As each facet of the rotating mirror sweeps the field, one of four signals is generated by the logic circuitry. If no specimen is encountered, a normal stage motion signal is generated. This causes the y positioning motor 54 to move the slide one step in the y direction so that another field of view can be scanned. This one step per mirror facet motion continues until a specimen is encountered by acquisition sensor 40. At this time a directional signal is produced. The directional signal indicates whether the specimen is to be moved to the right or left, ±x direction, in order to center the cell on the aperture. The x positioning motor 56 moves the slide in either the +x or the −x direction. The stage motors 54 and 56 are stepping motors which move the stage a predetermined distance for each applied pulse. This motion continues until the logic circuit produces a cell-centered signal on line 50. At this time all slide motion is halted, the cell specimen is centered in the aperture 28, and the vidicon 36 is enabled to allow it to make an analysis of the cell.

The operation can best be explained with reference to FIGS. 2A–2D. These FIGURES depict the image of a blood smeared slide. Included in this image is a specimen of interest, notably the blood cell 58 and other components such as red blood cells 60. The FIGURES depict the image in relation to aperture 28 as well as in relation to the field of view which is scanned and which is shown as the shaded areas. (It should be remembered that the image applied to aperture 28 is parfocal with the image scanned by rotating mirror 38. Therefore, it is accurate to depict the scan field of view as the shaded area in relation to aperture 28 in this manner.)

Figure 2A:
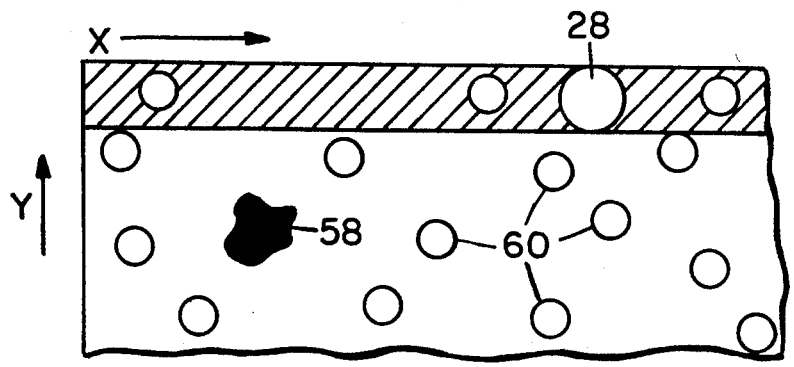
FIGS. 2A–2D depict the acquisition of a white blood cell.
Figure 2B:
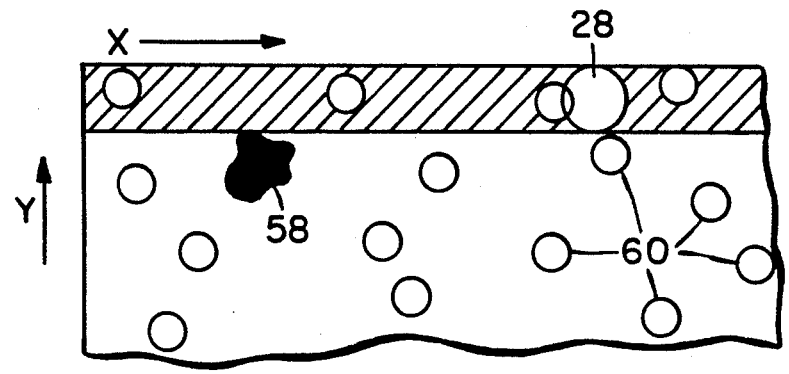
Figure 2C:
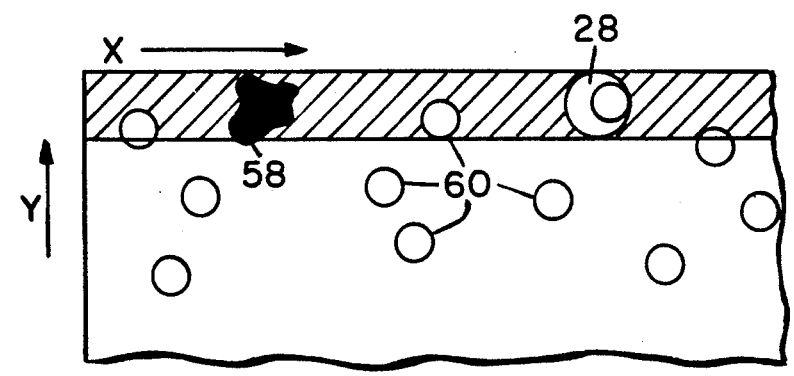
Figure 2D:
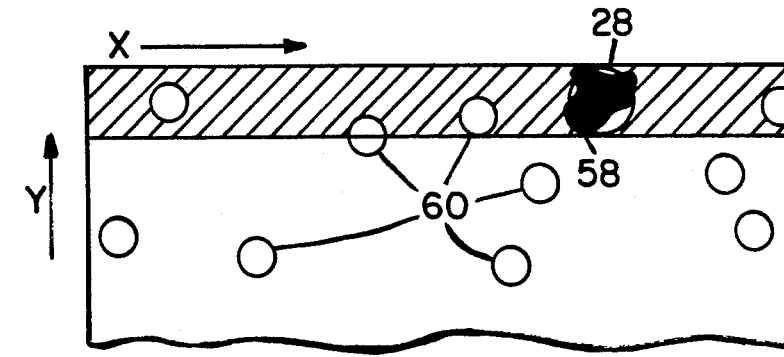

A first scan by one facet of mirror 38 is depicted in FIG. 2A. During scanning, less light reaches detector 40 when a white or red blood cell is encountered since light is absorbed thereby. Detector 40 therefore generates a positive signal on which are superimposed negative pulses corresponding to red and white blood cells. The pulse discriminator and shaper circuit of the present invention, which will be hereinafter described more fully, provides an output pulse only when a white blood cell is being scanned. During the scan depicted in FIG. 2A, a signal such as that illustrated in FIG. 3A is generated by detector 40, the negative going pulses illustrated therein representing only scanned red blood cells. Since no white blood cell is scanned, no pulse is generated by discriminator circuit 46 during the scanning period. Therefore, the logic circuitry produces a normal stage motion signal which moves the slide by one increment in the y direction. During the next scan depicted in FIG. 2B, the circuit 46 does not produce an acquisition pulse. Again, a normal stage motion signal moves the slide one increment in the y direction to the position depicted in FIG. 2C. During this scan, detector 40 generates a voltage such as that illustrated in FIG. 3B wherein pulse 66 represents a white blood cell. Circuit 46 therefore produces a pulse indicating that a white blood cell lies in the field of view of this scan. Further, the logic circuit detects that the cell lies to the left of aperture 28. Therefore, the logic circuit produces a directional signal which moves the slide in the +x direction. This directional signal is produced until the slide is positioned with cell 58 centered on aperture 28 as depicted in FIG. 2D.

The system of FIG. 1 is designed such that a stained white blood cell absorbs more light than a red blood cell, and the peak of pulse 66 of FIG. 3B should therefore be the most negative voltage generated by sensor 40 during the scan. However, an indicated hereinabove, nonuniform lighting conditions can cause a red blood cell in one part of the field to appear as dark as a white blood cell in another part of the field, and the light intensity from both types of cells can vary from time to time. The pulse discriminator and shaper circuit of the present invention can distinguish between pulses produced in response to red and white blood cells even under these adverse conditions. This circuit makes use of the fact that the light level through a cell is roughly proportional to the background light level. The cell simply absorbs a certain percentage of the light transmitted through the slide at that point, a white cell absorbing more than a red cell. The circuit to be hereinafter described uses the instantaneous background light level as a reference to determine the density of a cell and is thus very insensitive to the problems mentioned above.

Referring to FIG. 4, the amplified signal from amplifier 45 is fed to two channels, a first channel which comprises bandpass filter 70, non-inverting amplifier 72 and diode 74 and a second channel comprising inverting amplifier 76 and diode 78. Filter 70 passes only the band of frequencies contained in the red and white blood cell components of the signal. This reduces noise and eliminates the background information, but it also adds a positive going pulse to the end of each negative-going cell pulse as illustrated in FIG. 3C. Also pulses 81 and 83 are generated by the rising and falling edges of the background light signal. The signal is amplified by the non-inverting amplifier and then passes through diode 74 which eliminates the added positive-going pulses. This is done to make the waveform more intelligible to a serviceman. Waveform 90, which appears at the output of diode 74, is shown in FIG. 3D. Note that the background shape is gone, leaving only the cell pulses and the trailing edge pulse, which are negative going.

The function of the second channel is to amplify and invert the background waveform along with the signal pulses so that this voltage can be used as the trigger level that a cell pulse in the first channel must cross to provide an output pulse. The signal is amplified and inverted by amplifier 76; no bandpass filtering is employed, nor is any means required to remove the cell pulses. Diode 78 compensates for the voltage drop of diode 74 of the first channel, and it decouples resistor 84 from amplifier 76, which has a very low output impedance. Diode 76 becomes operative to perform this decoupling function when the voltage at the output of amplifier 76 becomes more positive than the bias voltage generated by resistors 82 and 84. The gain of amplifier 72 is greater than that of amplifier 76. The gain of the first channel is varied by adjusting potentiometer 80 so that only the white cell pulses of the first channel can cross their corresponding pulses in the second channel whereas the pulses produced by red cells cannot. Resistors 82 and 84 add a negative bias that shifts the second channel signal slightly negative so that the outputs from the two channels will not cross during the black or zero voltage portions of the signal.

The first and second channel output signals, which are applied to comparator 86, are shown in FIG. 3D as waveforms 90 and 92, respectively. Note that the background shape of the input signal is gone in waveform 90, due to filter 70, and that the positive peaks of the waveform shown in FIG. 3C have been removed by diode 74. Thus, only the negative going cell pulses and the trailing edge pulse remain in waveform 90. As illustrated in FIG. 3E, comparator 86 provides square output pulses 94 and 96 when the instantaneous voltage at the output of the first channel becomes about ¼ millivolt more negative than the instantaneous voltage at the output of the second channel, pulse 94 indicating the presence of a white blood cell. Pulse 96 is removed in logic circuit 52 since it does not occur during a gating signal generated in that circuit.

Since the pulse height of the signals produced by the cells is instantaneously proportional to the background amplitude, this circuit provides white cell detection that is independent of variations in the image field light intensity by effectively comparing the cell pulse height to the background level.

While a particular embodiment of the invention has been shown and described, various modifications are within the true spirit and scope of this invention. The appended claims are, therefore, intended to cover all such modifications.

We claim:
1. A pulse discriminator circuit for providing an output pulse when there appears at the input terminal thereof a pulse, the amplitude of which deviates from a background level of dc voltage by a predetermined amount, said circuit comprising:
   a voltage comparator for producing an output signal only when the voltage applied to a first terminal thereof exceeds that applied to a second terminal thereof,
   an inverting amplifier,
   first connecting means for connecting said input terminal to the input of said inverting amplifier,
   said connecting means for connecting the output of said inverting amplifier to the second terminal of said comparator,
   a non-inverting amplifier,
   a filter connected between said input terminal and the input of said non-inverting amplifier, said filter passing pulses while removing said background level of dc voltage, and
   third connecting means for connecting the output of said non-inverting amplifier to the first terminal of said comparator.

2. A system in accordance with claim 1, further comprising biasing means connected to said second comparator terminal for applying thereto a dc voltage of the same polarity as the background signal voltage appearing at the output of said inverting amplifier.

3. A system in accordance with claim 2 further comprising a diode connected between the output of said inverting amplifier and said biasing means, said diode preventing the flow of current from said biasing means to said inverting amplifier in the absence of a signal from said inverting amplifier.

4. A system in accordance with claim 3, wherein the gain of said non-inverting amplifier is greater than the gain of said inverting amplifier, and wherein said third connecting means comprises means for adjusting the level of the signal appearing at the output of said non-inverting amplifier.

5. In a system wherein an electrical signal is produced at a signal terminal, said signal having a varying background level of dc voltage, on which is superimposed pulses of different amplitudes, a circuit for generating an output pulse only when one of said superimposed pulses deviates from the background level adjacent thereto by a predetermined amount, said circuit comprising
   a voltage comparator for producing an output signal only when the voltage applied to a first terminal thereof exceeds that applied to a second terminal thereof,
   an inverting amplifier,
   first connecting means for connecting said signal terminal to the input of said inverting amplifier,
   second connecting means for connecting the output of said inverting amplifier to the second terminal of said comparator,
   a non-inverting amplifier,
   a filter connected between said signal terminal and the input of said non-inverting amplifier, said filter passing said pulses while removing said background level of dc voltage, and
   third connecting means for connecting the output of said non-inverting amplifier to the first terminal of said comparator.

6. In a system for producing an electrical output representing the optical characteristics of an analytical slide containing a specimen of interest, including:

conversion means producing said electrical output representing the optical characteristics of said slide, a rotating mirror, means for projecting an optical image of said analytical slide to said conversion means and to said rotating mirror, a light sensing device, said rotating mirror successively scanning a portion of said optical image across said light sensing device, said light sensing device producing an output representing the light absorption of the area of the slide being scanned, the output from said light sensing device comprising a varying background level of dc voltage on which is superimposed pulses of different amplitudes, pulse discriminating means connected to the output of said light sensing device and producing an acquisition pulse when the area of the slide being scanned contains a specimen of interest, means for producing a synchronizing pulse when said mirror is in a predetermined beam position, a positioning mechanism for positioning said slide, and logic circuitry responsive to said synchronizing pulse and to said acquisition pulse for producing control signals, said control signals being used to control said positioning mechanism to position said slide so that the image of a specimen of interest is centered on said conversion means, said pulse discriminating means being characterized in that it comprises:

a voltage comparator for producing an output signal only when the voltage applied to a first terminal thereof exceeds that applied to a second terminal thereof, an inverting amplifier, first connecting means for connecting the output of said light sensing device to the input of said inverting amplifier, second connecting means for connecting the output of said inverting amplifier to the second terminal of said comparator, a non-inverting amplifier, a filter connecting the output of said light sensing device to the input terminal of said non-inverting amplifier, said filter passing said pulses while removing said background level of dc voltage, and third connecting means for connecting the output of said non-inverting amplifier to the first terminal of said comparator.

* * * * *